(12) United States Patent
Noonan et al.

(10) Patent No.: US 7,430,608 B2
(45) Date of Patent: Sep. 30, 2008

(54) SYSTEM FOR PROCESSING DATA ACQUIRED FROM MULTIPLE MEDICAL DEVICES

(75) Inventors: Julianne Noonan, St. James, NY (US);
James Allan Schiel, Sanatoga, PA (US);
Mark E. Smith, Douglassville, PA (US);
Margie Forgione, Flourtown, PA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 544 days.

(21) Appl. No.: 10/114,642

(22) Filed: Apr. 2, 2002

(65) Prior Publication Data

US 2003/0105389 A1 Jun. 5, 2003

Related U.S. Application Data

(60) Provisional application No. 60/337,062, filed on Dec. 4, 2001.

(51) Int. Cl.
*G06F 15/16* (2006.01)
(52) U.S. Cl. .................. 709/230; 709/203; 709/246; 340/825.49; 340/825.52
(58) Field of Classification Search .............. 700/86, 700/17, 83, 52, 53; 709/205, 230, 24
See application file for complete search history.

(56) References Cited

U.S. PATENT DOCUMENTS

| | | | |
|---|---|---|---|
| 6,022,315 A | 2/2000 | Iliff | 600/300 |
| 6,206,829 B1 | 3/2001 | Iliff | 600/300 |
| 6,304,788 B1 * | 10/2001 | Eady et al. | 700/86 |

(Continued)

FOREIGN PATENT DOCUMENTS

EP 1 034 734 A1 9/2000

(Continued)

OTHER PUBLICATIONS

GE Medical Systems Monitoring Systems—Octanet Connectivity Device A Communication Bridge Between Peripheral Devices and Solar Monitors http://www.gemedicalsystems.com/monitor/products/modular/octanet_info.html, no date.

(Continued)

*Primary Examiner*—Yves Dalencourt
(74) *Attorney, Agent, or Firm*—Alexander Burke

(57) ABSTRACT

A system and a corresponding method processes data acquired from multiple medical devices located at one of multiple patient bed stations. A first data interface bi-directionally communicates with multiple medical devices in acquiring data, including patient related information, and acquisition device type identifier information from one of the multiple medical devices using a communication protocol selected from multiple communication protocols associated with different medical devices. A data processor incorporates the acquisition device type identifier information derived from the acquired data into a message in an Internet compatible format for communication to a remote device. A second data interface bi-directionally communicates with the remote device to convey the acquisition device type identifier information to the remote device in the Internet compatible format message and employs a predetermined source Internet communication address usable by the remote device to identify a source location of the message from a map associating Internet communication addresses and source locations.

19 Claims, 11 Drawing Sheets

U.S. PATENT DOCUMENTS

2002/0120676 A1* 8/2002 Biondi et al. .............. 709/203
2003/0072424 A1* 4/2003 Evans et al. ............ 379/106.02
2003/0200226 A1* 10/2003 Wells et al. .............. 707/104.1

FOREIGN PATENT DOCUMENTS

WO    WO 99/14882    3/1999
WO    WO 99/59472    11/1999

OTHER PUBLICATIONS

GE Medical Systems—Monitoring Systems HL7 Outbound http://www.gemedicalsystems.com/monitor/products/network/prism_h17.html, no date.

Philips Medical/Cardiac & Monitoring Systems, Connectivity http://www3.medical.philips.com/en-us/product_home/product_line/connectivity_detail.asp, no date.

Philips Medical/Cardiac & Monitoring Systems: Product Overview http://www3.medical.philips.com/en-us/product_home/product/devicelink_detail.asp, no date.

Plug-and-play Agilent Technologies www.agilent.com/healthcare, no date.

Welch Allyn Protocol/Press Releases, http://www.protocol.com/company/press000306flexnet.asp, no date.

University of Ulster Online—Faculty of Informatics, Development of an Internet application layer to support the transfer of medical data http://www.infc.ulst.ac.uk/cgi-bin/infdb/resprojview?projid=292, no date.

* cited by examiner

Data Router 106

Message formed by the M.D. 102-104 or the
data router 106 using the M.D. data format.      500

Message formed by the data router 106      600
using the Internet Protocol data format.

Message formed by the server 108 using
the Information System data format.        900

Message formed by the server 108 using the Internet Protocol data format.

1100

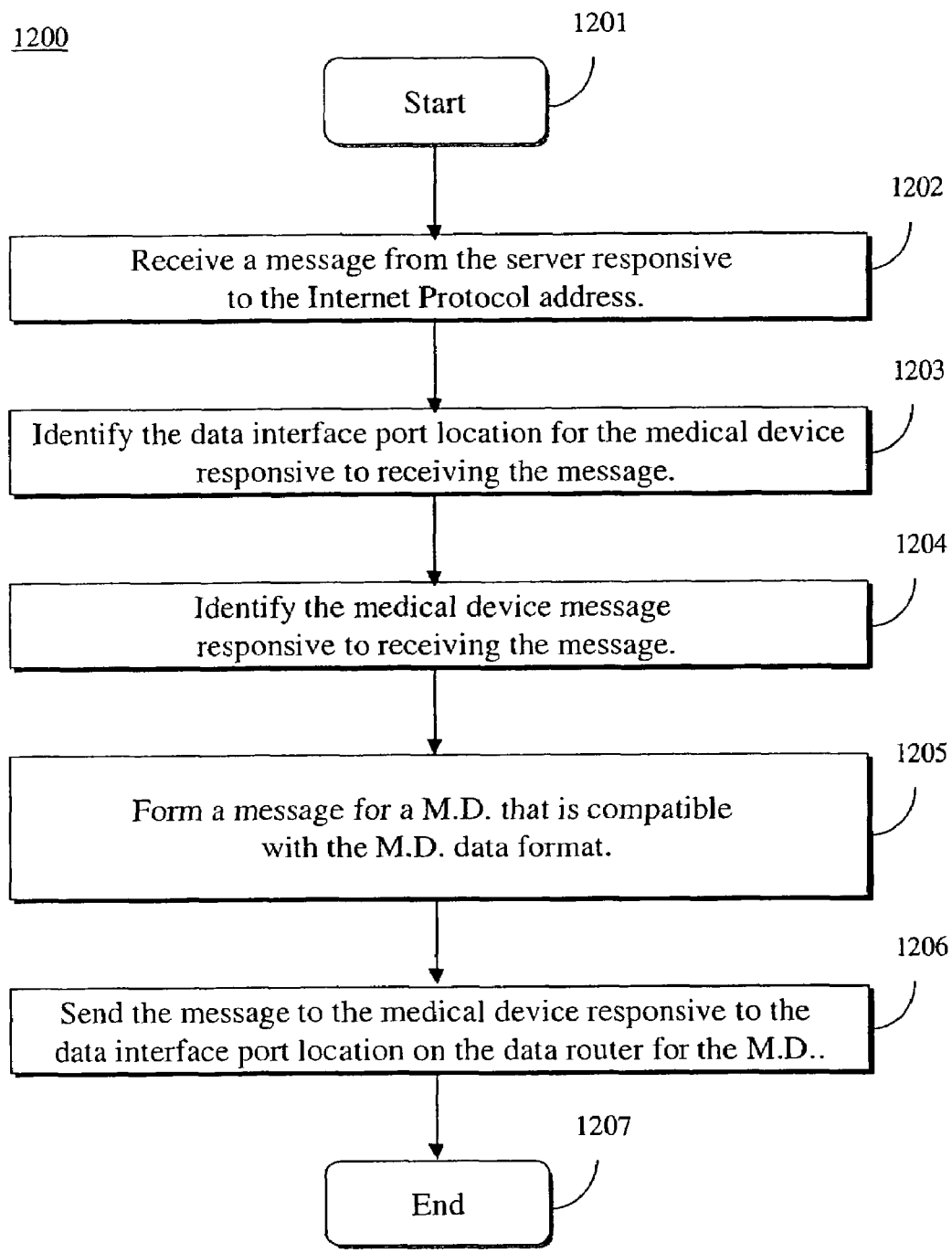

SYSTEM FOR PROCESSING DATA ACQUIRED FROM MULTIPLE MEDICAL DEVICES

CROSS-REFERENCE TO RELATED APPLICATIONS

The present application is a non-provisional application of provisional application having Ser. No. 60/337,062 filed by Julianne Noonan on Dec. 4, 2001.

FIELD OF THE INVENTION

The present invention generally relates to data processing systems. More particularly, the present invention relates to a system for processing data acquired from multiple medical devices.

BACKGROUND OF THE INVENTION

A healthcare data processing system typically communicates healthcare data between one or more medical devices and one or more information systems for a healthcare provider such as a hospital. The medical devices are typically located at a patient's bedside in the patient's room and monitor the status of the heath of the patient, such as the patient's pulse rate, by generating healthcare data. The information systems may be located inside or outside of a person's room and monitor the healthcare data provided by the medical devices and other information systems for one or more patients.

Standardized data interface formats, such as a Medical Information Bus (MIB), permit the information systems to identify the source of the medical device providing the healthcare data. The Medical Information Bus (MIB) is typically used for locally interconnecting the medical devices in a patient's room. However, the majority of the medical devices presently available on the market do not conform to such a standardized data interface format. Hence, the information systems, such as a computer with a monitor, are typically located inside of a patient's room and typically require hardware and/or software drivers that interface with the various data interface formats provided by the medical devices.

A problem with this configuration is that new hardware and/or software drivers need to be installed in the information system every time a new medical device is added or changed. To overcome this problem, individual hardware interface drivers, containing hard-coded circuits, are connected between each medical device and the information system to convert the data format of each medical device to a standard data format that can be recognized by one hardware and/or software driver installed in the information system. These hardware interface drivers merely shift the interface driver functionality from inside the information system to outside the information system. Therefore, the problem remains that each new medical devices that is added or changed requires a new hardware interface driver, which is costly and time consuming to install and maintain.

Some healthcare data processing systems provide an information system, such as a computer with a monitor, which is located outside of a patient's room and typically provides centralized monitoring for one or more patients. However, this information system also requires that new hardware and/or software drivers need to be installed in the information system every time a new medical device is added, which is costly and time consuming to install and maintain.

It would be desirable to have a healthcare data processing system wherein new medical devices could be added or changed, without requiring the installation of new hardware and/or software drivers, to permit a "plug and play" solution. It would further be desirable to have a healthcare data processing system that could provide more information than that typically provided by the medical devices. Preferably, the information would include the source of the location of the healthcare data, such as the patient's room, bed, and name.

Accordingly, there is a need for a system for processing data acquired from multiple medical devices that overcomes the disadvantages of the conventional healthcare data processing system by providing a "plug and play" solution and by adding information associated with the healthcare data.

SUMMARY OF THE INVENTION

According to one aspect of the present invention, a system and a corresponding method processes data acquired from multiple medical devices located at one of multiple patient bed stations. A first data interface bi-directionally communicates with multiple medical devices in acquiring data, including patient related information, and acquisition device type identifier information from one of the multiple medical devices using a communication protocol selected from multiple communication protocols associated with different medical devices. A data processor incorporates the acquisition device type identifier information derived from the acquired data into a message in an Internet compatible format for communication to a remote device. A second data interface bi-directionally communicates with the remote device to convey the acquisition device type identifier information to the remote device in the Internet compatible format message and employs a predetermined source Internet communication address usable by the remote device to identify a source location of the message from a map associating Internet communication addresses and source locations.

These and other aspects of the present invention, are further described with reference to the following detailed description and the accompanying figures, wherein the same reference numbers are assigned to the same features or elements illustrated in different figures. Note that the figures may not be drawn to scale. Further, there may be other embodiments of the present invention explicitly or implicitly described in the specification that are not specifically illustrated in the figures and visa versa.

BRIEF DESCRIPTION OF THE DRAWINGS

FIG. 12 illustrates a method performed by the server to medical device data router, as shown in FIG. 2, in accordance with a preferred embodiment of the present invention.

DETAILED DESCRIPTION OF THE PREFERRED EMBODIMENTS

Figure 1:
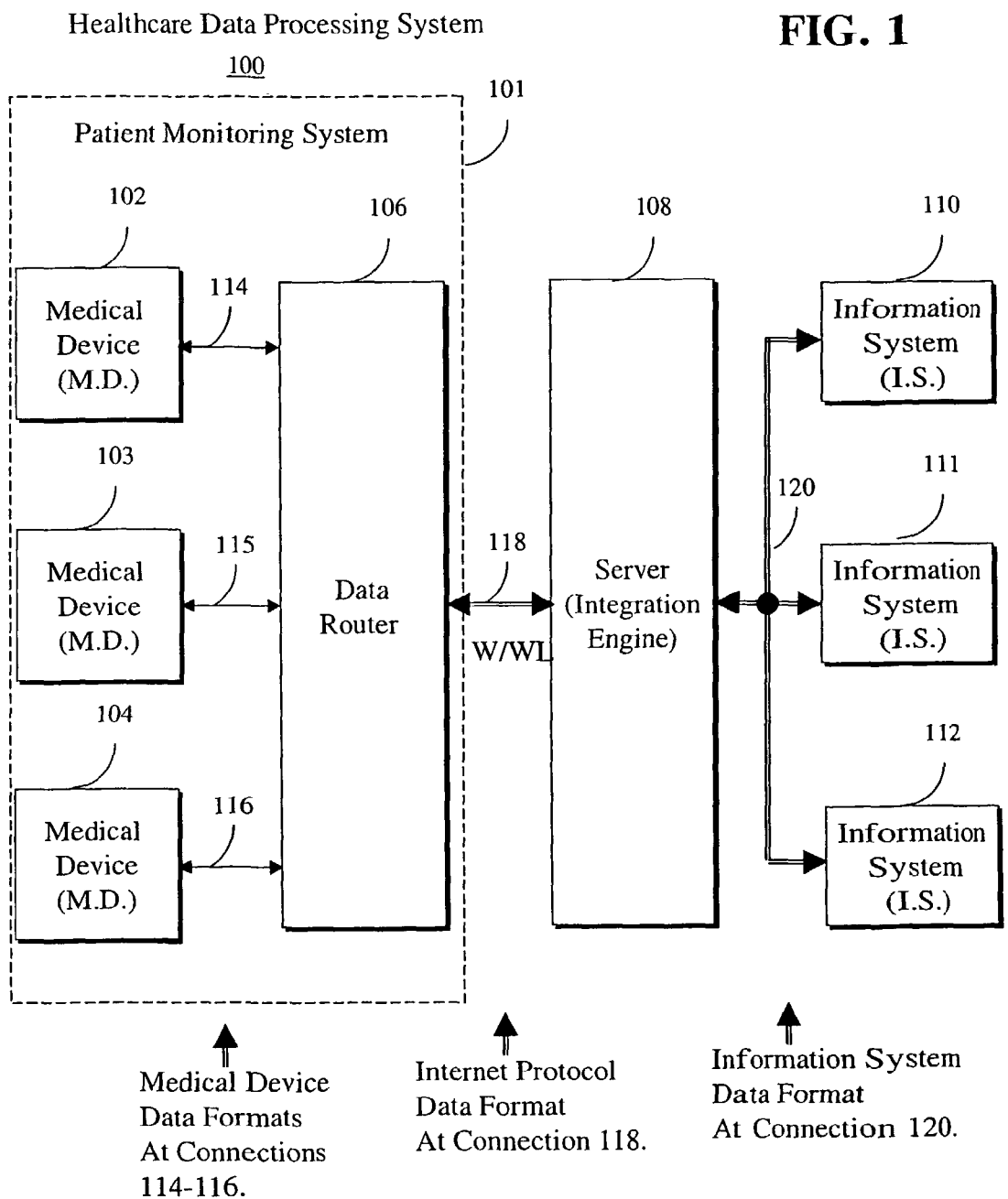
FIG. 1 illustrates a block diagram of a healthcare data processing system in accordance with a preferred embodiment of the present invention.

FIG. 1 illustrates a block diagram of a healthcare data processing system 100 in accordance with a preferred embodiment of the present invention. Preferably, the healthcare data processing system 100 is intended for use by a healthcare provider that is responsible for monitoring the health and/or welfare of people in its care. Examples of healthcare providers include, without limitation, a hospital, a nursing home, an assisted living care arrangement, a home health care arrangement, a hospice arrangement, a health care clinic, a physical therapy clinic, a chiropractic clinic, and a dental office. In the preferred embodiment of the present invention, the healthcare provider is a hospital. Examples of the people being serviced by the healthcare provider include, without limitation, a patient, a resident, and a client.

The healthcare data processing system 100 generally includes one or more patient monitoring systems 101, a server 108, and one or more information systems 110-112. The patient monitoring system 101 further includes one or more medical devices (M.D.) 102-104 and a data router 106.

The server 108 is preferably implemented as a personal computer or local server. The server 108 also preferably embodies hardware and/or software provided by a system that converts the data format and processes the data between different computer systems.

The information systems 110-112 are systems that need access to data related to the health and/or welfare of people in the care of the healthcare provider. Examples of the information systems 110-112 include, without limitation, a records system, a nurse's station system, a pharmacy system, a lab system, a radiology system, an accounting system, and a billing system.

The medical devices 102-104 are devices that monitor the health and/or welfare of the people in the care of the healthcare provider. In the preferred embodiment of the present invention, the medical devices 102-104 are bedside medical devices that provide patient related information. The health and/or welfare of the people include, without limitation, the status of a person's biological condition, the status of a person's environment, the location of a person, and the status and/or position of a machine used by a person. The status of a person's biological condition includes, without limitation, the measurable bodily functions of a person, such as heart rate, blood pressure, temperature, the sounds made by a person (i.e., audio), the movement of a person (i.e. video), the aroma of a person (i.e., smell), and the feel of a person (i.e., touch). Examples of the medical devices 102-104 include, without limitation, a heart rate monitor, a blood pressure monitor, a fetal monitor, a medication dispensing monitor, a temperature sensor for the person, a temperature sensor the person's environment, a location sensor in a person's bed or on the person, a machine sensor that determines the position of a person's bed, for example, a video camera, and an audio input, such as a microphone.

The patient monitoring system 101 is electrically coupled to the server 108 via a communication path 118. The communication path 118 is preferably adapted to use an Internet Protocol (I.P.) data format, otherwise called an I.P. protocol, and IP addresses. Examples of the I.P. addresses include, without limitation, Transmission Control Protocol Internet Protocol (TCPIP) address, an I.P. address, a Universal Resource Locator (URL), and an electronic mail (Email) address. The communication path 118 may be formed as a wired or wireless (W/WL) connection. Preferably, the communication path 118 is formed as a wired connection. In the case of a wired connection, the I.P. address is preferably assigned to a physical location of the termination point of the wire, otherwise called a jack. The jack is mounted in a fixed location relative to the person receiving the health care. The fixed location depends on the type of healthcare provider arrangement, as described above. In the preferred embodiment of the present invention, wherein the healthcare provider is a hospital, the fixed location is mounted at a patient's bedside station, such as in a wall next to the patent's bed. Alternatively, the data router 106 may be assigned an I.P. address. In this case the data router 106 itself is preferably mounted in a fixed location relative to the person receiving the health care, such as on or in a wall next to the patient's bed. In the case of a wireless connection, the I.P. address is preferably assigned to the device router 106, since the device router 106 would be mobile. The wireless connection permits the person receiving the healthcare to be mobile beyond the distance permitted with the wired connection.

The server 108 is electrically coupled to the information systems 110-112 via a communication path 120. The server 108, also referred to as a remote device, is preferably implemented as a personal computer or a workstation. The communication path 120 is preferably adapted to use one or more information system data formats, depending on the type and/or configuration of the information systems 110-112. The communication path 120 is preferably adapted to use one or more information system data formats, otherwise called protocols, depending on the type and/or configuration of the information systems 110-112. Examples of the information system data formats include, without limitation, an RS232 protocol, an Ethernet protocol, a Medical Interface Bus (MIB) compatible protocol, the I.P. data format, as described above, a Local Area Network (LAN) protocol, a Wide Area Network (WAN) protocol, an IEEE bus compatible protocol, and an Health Level Seven (HL7) protocol. Note any particular one of these protocols may be implemented the same or different among various similar or different information systems 110-112.

In the patient monitoring system 101, each of the medical devices 102-104 is electrically coupled to the data router 106 via communication paths 114-116, respectively. Preferably, the data router 106 is configured to receive one or more, as represented by medical devices 102-104. Each of the communication paths 114-116 is preferably adapted to use one or more medical device data formats, otherwise called protocols, depending on the type and/or configuration of the medical devices 102-104. Examples of the medical device data formats include, without limitation, the same protocols described above with reference to the information system data formats. Note any particular one of these protocols may be implemented the same or different among various similar or different medical devices manufactured by different manufacturers. In the preferred embodiment of the present invention, the medical device data format is the RS232 protocol, wherein different manufacturers implement the RS232 protocol in a different way for similar or different medical devices.

Figure 2:
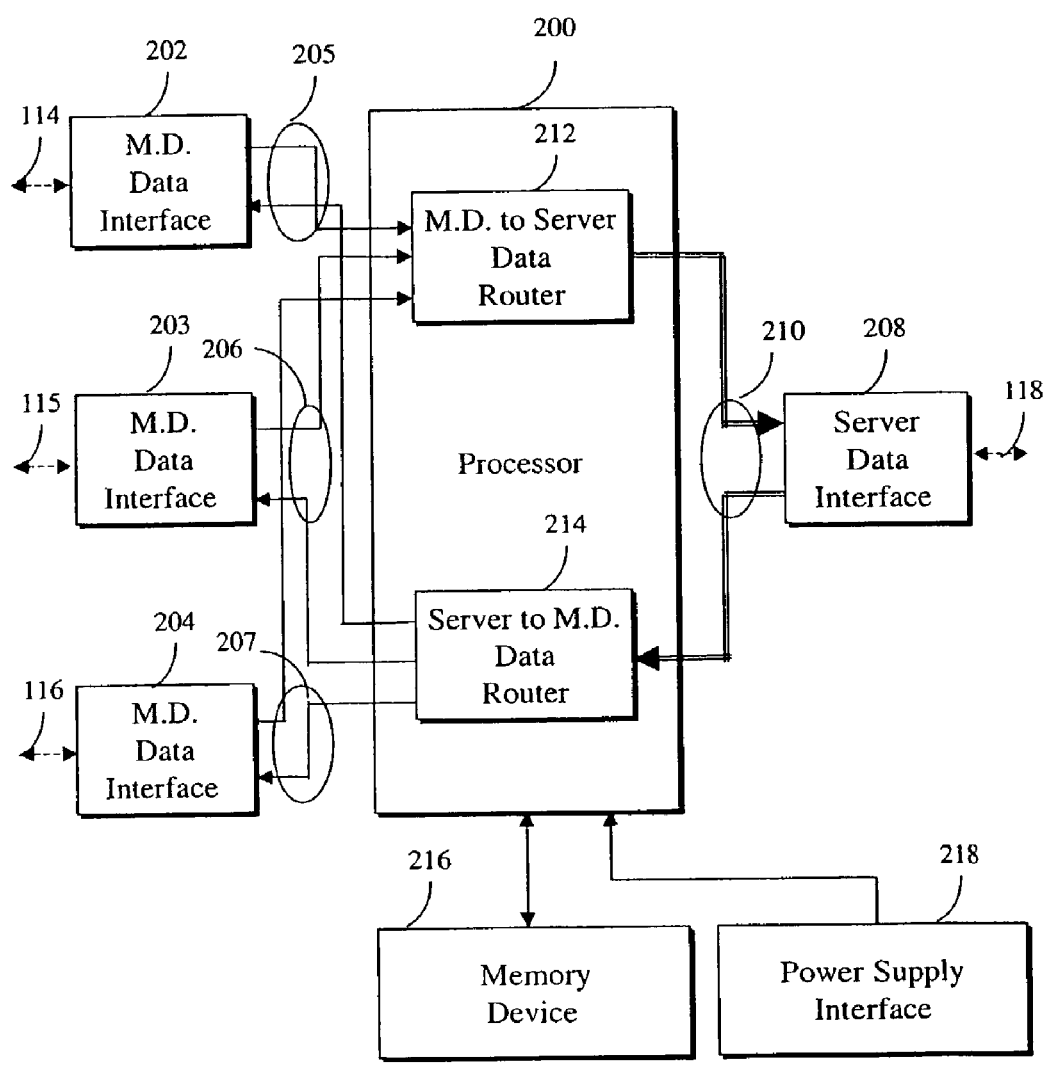
FIG. 2 illustrates a block diagram of the data router, as shown in FIG. 1, in accordance with a preferred embodiment of the present invention.

FIG. 2 illustrates a block diagram of the data router 106, as shown in FIG. 1, in accordance with a preferred embodiment of the present invention. The data router 106 generally includes a processor 200, medical device data interfaces 202-204, a server data interface 208, a memory device 216 and a power supply interface 218. The processor 200 further includes a medical device to server data router 212 and a server to medical device data router 214. The medical device data interfaces 202-204 and the server data interface 208 may also be referred to as an interface processor. The data router 106 may alternatively be referred to as a data processor, a data converter, a data consolidator, a data formatter, and the like.

The medical device data interfaces 202-204 are electrically coupled to the medical device to server data router 212 and the server to medical device data router 214 via communication paths 205-207, respectively. The medical device to server data router 212 and the server to medical device data router 214 are electrically coupled to the server data interface 208 via the communication path 210. In the preferred embodiment of the present invention, each of the communication paths 205, 206, 207 and 210 are bi-directional communication paths over a common connection, but are shown as separate inputs and outputs connecting to the respective data routers 212 and 214 for the sake of clarity and understanding.

The medical device data interfaces 202-204 provide a physical interface, otherwise called a jack, for receiving data from and sending messages to the medical devices 202-204, respectively, over the communication paths 114-116, respectively. The server data interface 208 also provides a physical interface, otherwise called a jack, for receiving messages from and sending messages to the server 108 over the communication path 118.

The medical device to server data router 212 routes data from any one of the medical devices 202-204 to the server 108 by performing two functions. The first function is to convert the data format or the protocol of the messages from the medical device data format to the I.P. data format. Although the data format of the messages is converted, the information content of the messages is not changed. The second function is to append fields of information to the converted messages related to the source of the messages sent. Such source information permits the server to identify the model of the data router sending the messages, the make and model of the medical device sending the messages, and the data interface port location on the data router 106 of the medical device sending the messages. In the specific cases of the wired communication path 118, wherein the I.P. address is assigned to the data router 106 and not assigned to the jack, or the wireless communication path 118, as described above, the medical device to server data router 212 would also append a field of information representative of the I.P. address of the data router 106. The operation of the medical device to server data router 212 is described in further detail with reference to FIGS. 4, 5 and 6.

The server to medical device data router 214 routes data from the server 108 to any one of the medical devices 202-204 by performing two functions. The first function is to convert the data format or the protocol of the messages from the I.P. data format to the medical device data format. Although the format of the messages is converted, the information content of the messages is not changed. The second function is to remove fields of information from the messages that are related to the destination of the messages. Such destination information permits the data router 106 to receive the messages responsive to the I.P. address of the data router 106, and to identify the data interface port location on the data router 106 for the medical device. The operation of the server to medical device data router 214 is described in further detail with reference to FIGS. 10, 11 and 5.

Hence, the server to medical device data router 214 and the medical device to server data router 212 complement each other to route the messages in both directions through the data router 106 by converting the format of the data between the medical device data format and the I.P. data format, and by adding or removing fields of information related to the source or destination, respectively, of the messages. Note that the server to medical device data router 214 and the medical device to server data router 212 are shown as two separate functional blocks for the sake of clarity and understanding, but are preferably implemented in one software program.

The memory device 216 is electrically coupled to the processor 200 and may comprise read only memory (ROM) and/or random access memory (RAM) in their various available forms. The memory 216 is preferably physically integrated with the processor 200, but, alternatively, may be physically separate from the processor 200, as each arrangement is well known in the art.

The power supply interface 218 is electrically coupled to the processor 200. In the preferred embodiment of the present invention, wherein the communication path 118 is a wired connection, the power supply interface 218 connects to an alternating current (AC) power supply located in relatively close proximity to the jack for the communication path 118, to minimize the length of the power cord. Alternatively, when the communication path 118 is a wireless connection, the power supply interface 218 would connect to a direct current (DC) power supply, such as a battery, because of the need for a mobile power supply. In this case, the DC power supply may be physically carried with the data router 106, such as inside or outside a housing of the data router 106, or may be connected to the power supply interface 218 via a short power cable.

Figure 3:
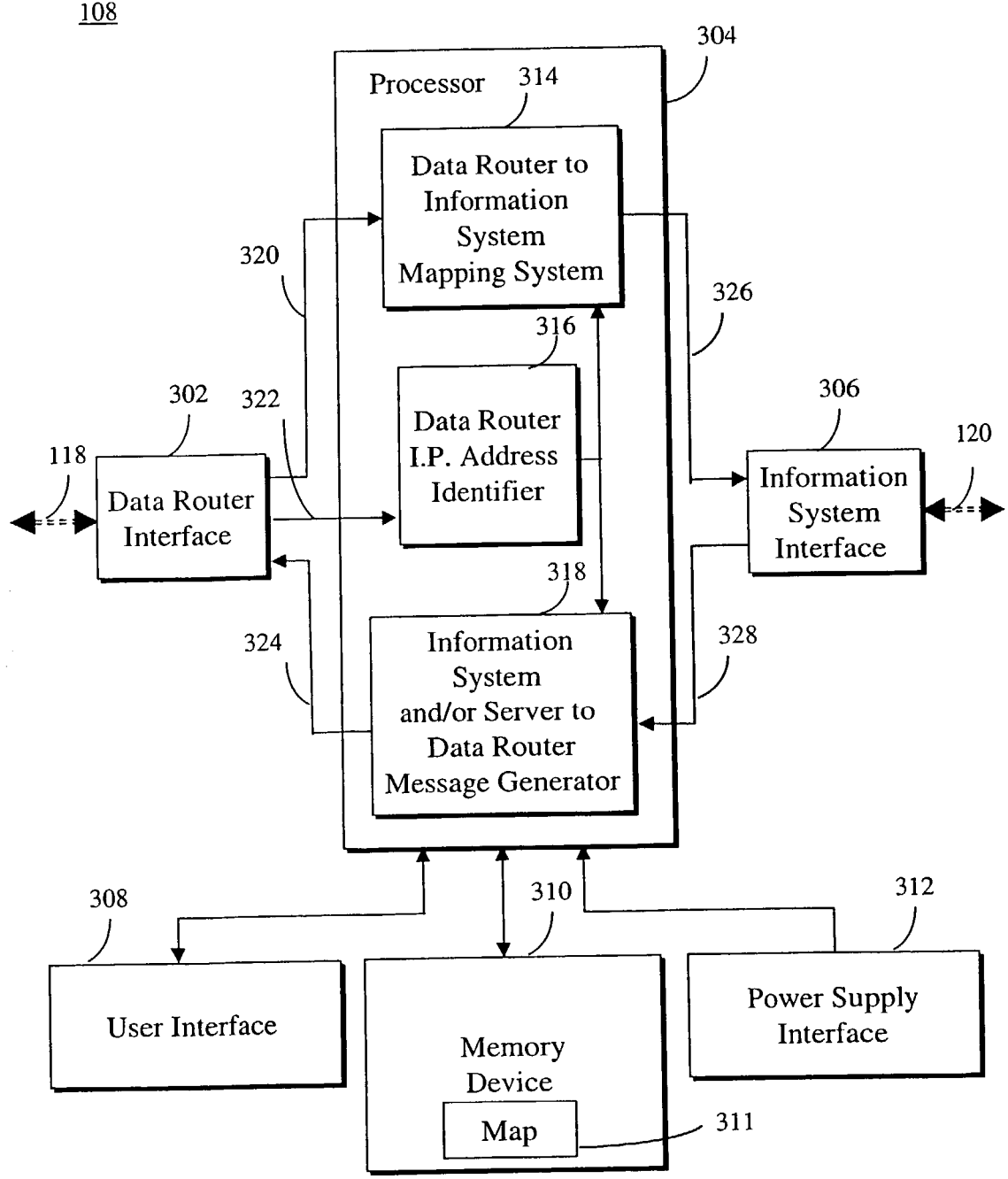
FIG. 3 illustrates a block diagram of the server, as shown in FIG. 1, in accordance with a preferred embodiment of the present invention.

FIG. 3 illustrates a block diagram of the server (integration engine) 108, as shown in FIG. 1, in accordance with a preferred embodiment of the present invention. The server 108 generally includes a data router interface 302, a processor 304, an information system interface 306, a user interface 308, a memory device 310 and a power supply interface 312. The processor 304 further includes a data router to information system mapping system 314, a data router I.P. address identifier 316, and an information system and/or server to data router message generator 318.

The data router interface 302 is electrically coupled to the mapping system 314 via communication path 320 and to the I.P. address identifier 316 via communication path 322 via communication path 324. The I.P. address identifier 316 is electrically coupled to the mapping system 314 and to the message generator 318. The mapping system 314 is electrically coupled to the information system interface 306 via the communication path 326. The information system interface 306 is electrically coupled to the message generator 318 via the communication path 328. The message generator 318 is electrically coupled to the data router interface 302 via the communication path 324. In the preferred embodiment of the present invention, the communication paths 320, 322 and 324 together form a bi-directional communication path over a common connection, but are shown as separate inputs and outputs connecting to the respective mapping system 314, I.P address identifier 316 and the message generator 318 for the sake of clarity and understanding. Likewise, in the preferred embodiment of the present invention, the communication paths 326 and 328 together form a bi-directional communication path over a common connection, but are shown as separate inputs and outputs connecting to the respective mapping system 314 and the message generator 318 for the sake of clarity and understanding.

The data router interface 302 provides a physical interface, otherwise called a jack or a network connection, for receiving data from and sending messages to the data router 106 over the communication path 118. The information system interface 306 also provides a physical interface, otherwise called a jack or a network connection, for receiving messages from and sending messages to the information systems 110-112 over the communication path 120.

The I.P. address identifier 316 identifies the I.P. address, otherwise known as a predetermined source Internet address, associated with the data router 106. The I.P. address corresponds to a physical location, otherwise known as a source location, of the data router 106 that is stored in the memory 310 of the server 108. The I.P. address is used by the mapping system 314 to append source information to the messages sent to the information systems 110-112, and by the message generator 318 to append destination information to the messages sent to the data router 106. The operation of the I.P. address identifier 316 is described in further detail with reference to FIG. 7.

The mapping system 314 routes messages from the data router interface 302 to the information system interface 306 by performing two functions. The first function is to convert the data format or the protocol of the messages from the I.P. data format to the information system data format. Although the data format of the messages is converted, the information content of the messages is not changed. The information system data format of the messages is well known to those skilled in the art of healthcare information systems. The second function is to route the formatted data to the appropriate information system 110-112 with additional appropriate corresponding information, if it is not already included in the content of the message. The additional information includes, without limitation, patient related information, a patient's physical location (e.g., room number and/or bed location in the room) corresponding to the I.P. address of the jack or data router 106, the make and/or model of the medical device that sent the message, a time and/or date stamp of when the message was sent, a patient's name corresponding to the I.P. address of the jack or data router 106, and the units of the data being sent. In the preferred embodiment of the present invention, the mapping system 314 associates, using a map 311 stored in the memory device 310, the predetermined source Internet address to the source location. The additional information that is included is preferably programmable and definable by a user or technician of the server 108 via the user interface 308. The operation of the medical device to server data router 212 is described in further detail with reference to FIGS. 6 and 8.

The message generator 318 forms or routes messages from the server 108 or the information systems 110-112, respectively, to the data router 106 by performing two functions. The first function is to convert the data format or the protocol of the messages from the information system data format to the I.P. data format. Although the format of the messages is converted, the information content of the messages is not changed. The second function is to append fields of information to the converted messages that is related to the destination of the messages. Such destination information includes the I.P. address of the data router 106, and the data interface port location on the data router 106 for the medical device. The operation of the message generator 318 is described in further detail with reference to FIGS. 7 and 1000.

Hence, the mapping system 314 and the message generator 318 complement each other to route the messages in both directions through the server 108 by converting the format of the data between the information system data format and the I.P. data format, and by adding fields of information related to the source or destination, respectively, of the messages. Note that the mapping system 314, the I.P. address identifier 316, and the message generator 318 are shown as three separate functional blocks for the sake of clarity and understanding, but are preferably implemented in one software program.

The memory device 310 is electrically coupled to the processor 304 and may comprise read only memory (ROM) and/or random access memory (RAM) in their various available forms. The memory 310 is preferably physically integrated with the processor 304, but, alternatively, may be physically separate from the processor 304, as each arrangement is well known in the art. The mapped information, described above, is stored in the memory device 310.

The power supply interface 312 is electrically coupled to the processor 304. In the preferred embodiment of the present invention, the power supply interface 312 connects to an alternating current (AC) power supply.

Figure 4:
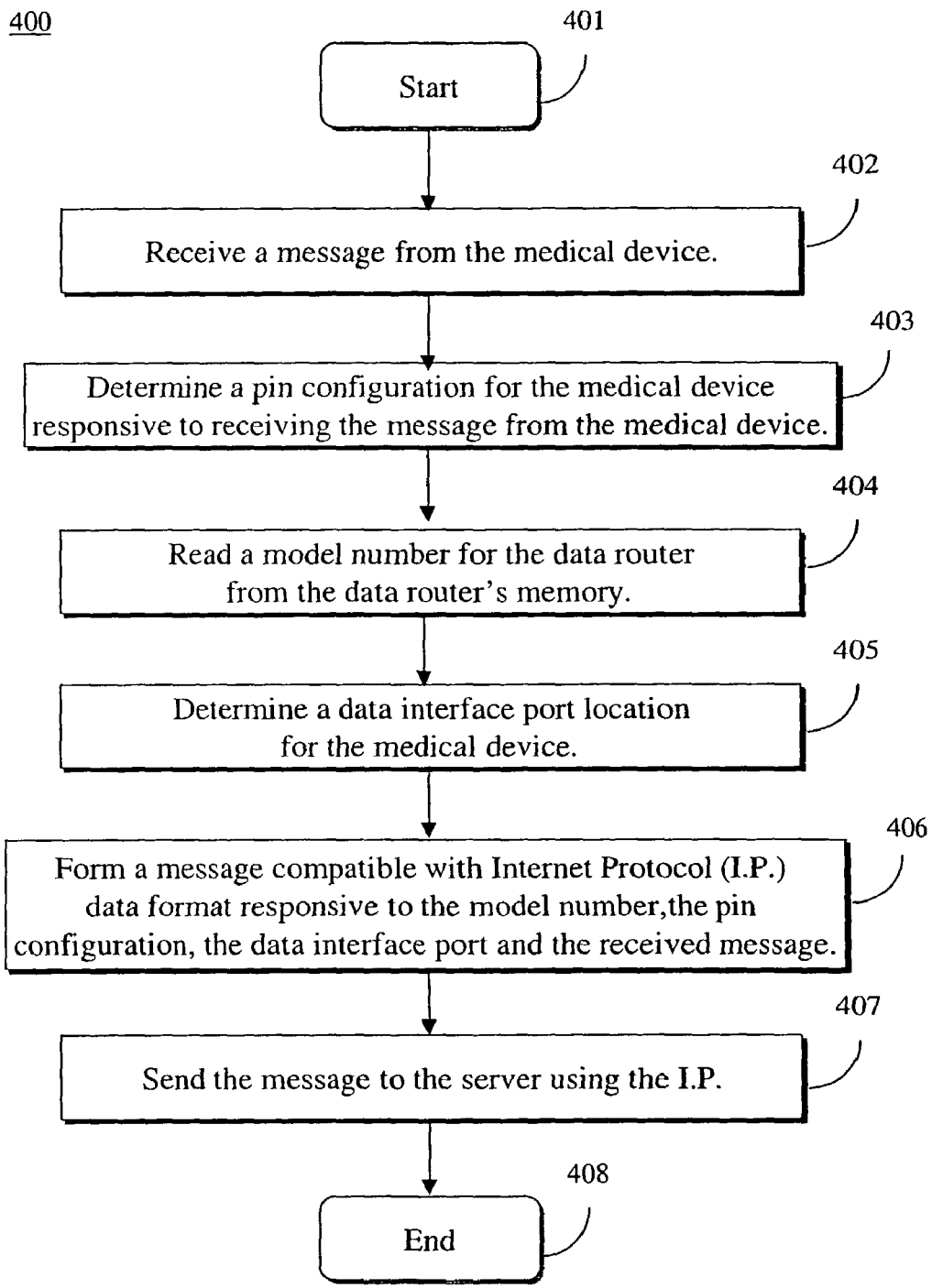
FIG. 4 illustrates a method performed by the medical device to server data router, as shown in FIG. 2, in accordance with a preferred embodiment of the present invention.
Figure 5:
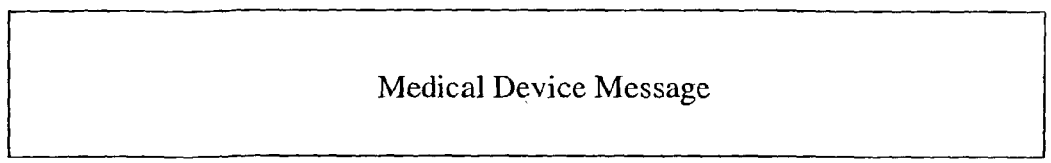
FIG. 5 illustrates a message formed by one of the medical devices, as shown in FIG. 1, in accordance with a preferred embodiment of the present invention.
Figure 6:
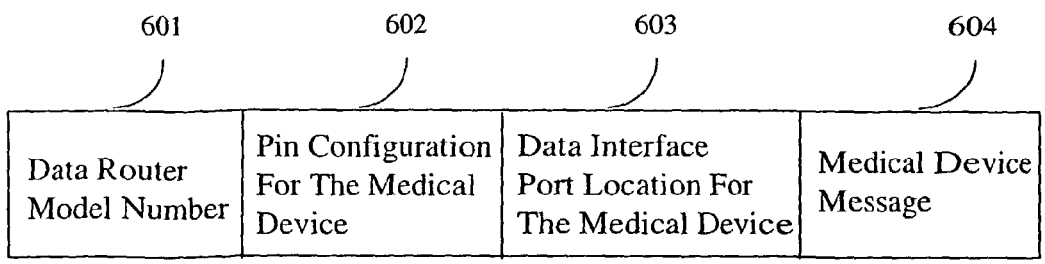
FIG. 6 illustrates a message formed by the data router, as shown in FIGS. 1 and 2, using the method, as shown in FIG. 4, in accordance with a preferred embodiment of the present invention.

FIGS. 4, 5 and 6 are described together. FIG. 4 illustrates a method 400 performed by the medical device to server data router 212, as shown in FIG. 2, in accordance with a preferred embodiment of the present invention. FIG. 5 illustrates a message 500 formed by one of the medical devices, as shown in FIG. 1, in accordance with a preferred embodiment of the present invention. FIG. 6 illustrates a message 600 formed by the data router 106, as shown in FIGS. 1 and 2, using the method, as shown in FIG. 4, in accordance with a preferred embodiment of the present invention. The message 600 has the I.P. data format.

At step 401, the method 400 starts.

At step 402, the method 400 receives the message 500, as shown in FIG. 5, from one of the medical device 102-104 in a medical device data format. The message 500 contains patient related information provided by the medical device 102-104, such as the person's heart rate, units of the measurement, as is well known in the art to those skilled in the art of medical devices. The medical device data format is well known in the art to those skilled in the art of medical devices. In the preferred embodiment of the present invention, the medical device data format is generated by controlling the data on one or more of the sixteen pins provided on a conventional RS232 cable connection.

At step 403, the method 400 determines a pin configuration for the medical device 102-104 responsive to receiving the message 500 from the medical device 102-104. The pin configuration corresponds to the one or more of the sixteen pins provided on a conventional RS232 cable connection that carry data. Preferably, the pin configuration is determined by the processor 200 sniffing or scanning the pins at the medical device data interface 202-204 to detect any data activity on the pins. Presently, the various medical device 102-104 used in a particular healthcare setting are required to have different pin configurations so that the messages from one medical device 102-104 will not be confused with the messages from another medical device 102-104. Hence, various determined pin configurations correspond to various makes, models, and/or types of medical device 102-104 in a particular healthcare setting. Alternatively, another characteristic identifying the medical device 102-104 may be a code included in the medical device message 500.

At step 404, the method 400 reads a model number of the data router 106 from the data router's memory 216. The model number of the data router 106 identifies the particular make, model and/or type of data router 106. The model number is stored in the memory 216 of the data router 106 when the data router 106 is manufactured.

At step 405, the method 400 determines a data interface port location on the data router 106 for the medical device 102-104. The processor 200 determines data interface port location by the electrically detecting which medical device data interface 202-204 received the message from the medical device 102-104.

At step 406, the method 400 forms the message 600, as shown in FIG. 6, that is compatible with the I.P. data format responsive to the model number, the pin configuration, the data interface port location for the data router 106, and the received message 500. In FIG. 6, the message 600 includes fields of information for the data router model number field 601, the pin configuration for the medical device field 602, the data interface port location for the data router 106 field 603, and the medical device message field 604. The particular order of the fields of information may vary according to design considerations. The pin configuration for the medical device field 602 and the medical device message field 604 are provided in the message 600 so that the server 108 knows what make, model and/or type of medical device 102-104 sent the message. The data router model number field 601 is included so that the server 108 knows what version of the data router 106 sent the message, which may be useful information when the data routers 106 are upgraded with newer models having different or more advanced capabilities. The data interface port location for the data router 106 field 603 is included so that the server knows which data interface port location on the data router sent the message 600, which is useful information for the server 108 to be able to send a message back to the medical device 102-104. As mentioned above, in the case of the communication path 118 being a wired connection, the I.P. address preferably corresponds to the location of the jack in the network. Alternatively, in the case of the communication path 118 being a wireless connection, the I.P. address of the data router 106 would also be added to the message 600 as an additional field of information. In both the wired and wireless cases, the I.P. address is useful information for the server 108 to be able to send a message back to the medical device 102-104 via the data router 106. An example of the message 600, as shown in FIG. 6, is as follows:

1.0/1-3-6/2/O2Hb/13.4%, wherein 1.0 is the model number of the data router 106, 1-3-6 is the pin configuration of the medical device 102-104, 2 is the data interface port location on the data router 106, and O2Hb/13.4% is the medical device message.

At step 407, the method 400 sends the message 600 to the server 108 using the I.P. data format.

At step 408, the method 400 ends.

Figure 7:
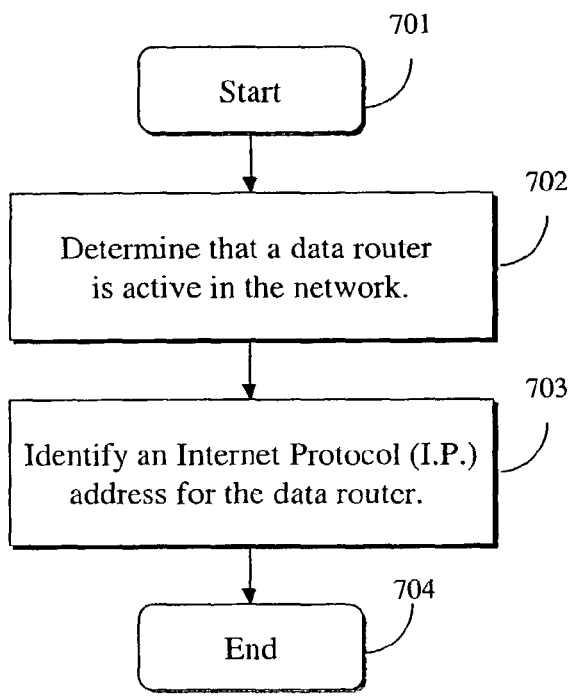
FIG. 7 illustrates a method performed by the Internet Protocol (I.P.) address identifier in the server, as shown in FIG. 3, in accordance with a preferred embodiment of the present invention.

FIG. 7 illustrates a method 700 performed by the I.P. address identifier 316 in the server 108, as shown in FIG. 3, in accordance with a preferred embodiment of the present invention.

At step 701, the method 700 starts.

At step 702, the method 700 determines that a data router 106 is active in the network. Preferably, I.P. address identifier 316 in the server 108 makes this determination when the data router 106 is plugged into the jack and when power is applied to the data router 106.

At step 703, the method 700 identifies the I.P. address for the data router 106 responsive to the step 702 of determining that the data router 106 is active in the network. Alternatively, when the communication path 118 is a wireless connection, steps 702 and 703 are performed when the data router 106 request service from the system and provides the I.P. address associated with the data router 106.

At step 704, the method 700 ends.

Figure 8:
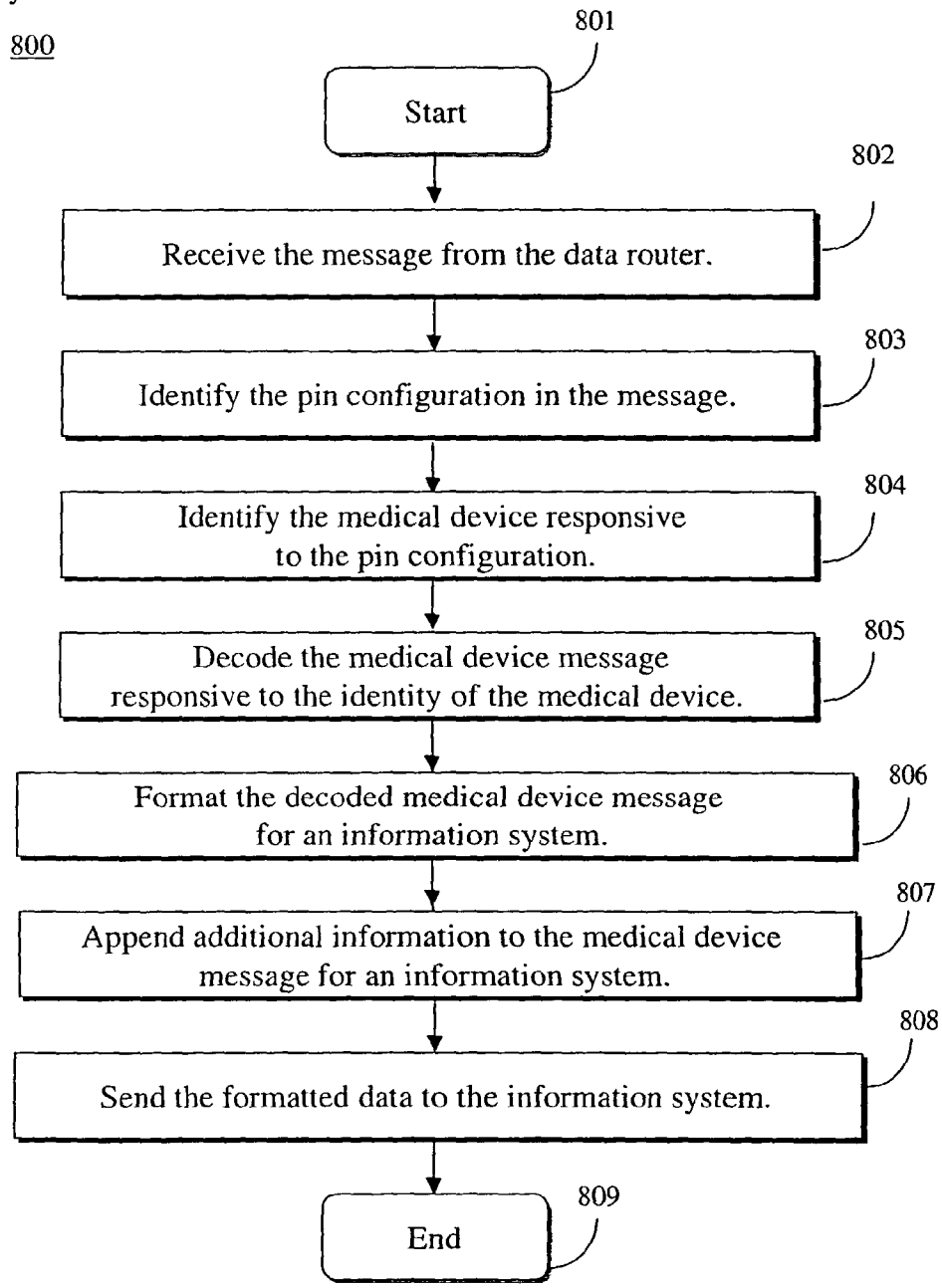
FIG. 8 illustrates a method performed by the mapping system in the server, as shown in FIG. 3, in accordance with a preferred embodiment of the present invention.
Figure 9:
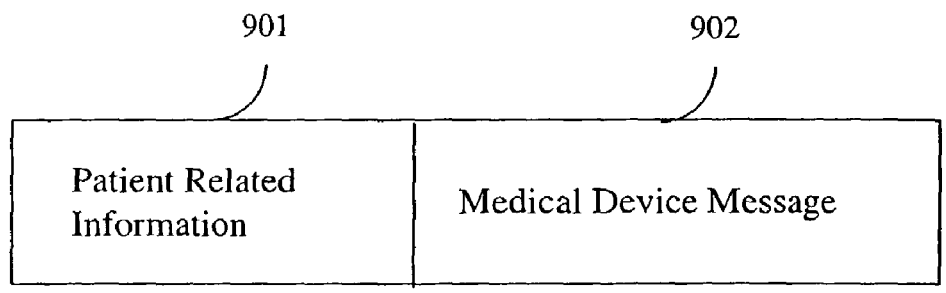
FIG. 9 illustrates a message formed by the mapping system in the server, as shown in FIG. 3, using the method, as shown in FIG. 8, in accordance with a preferred embodiment of the present invention.

FIGS. 8 and 9 are described together. FIG. 8 illustrates a method 800 performed by the mapping system 314 in the server 108, as shown in FIG. 3, in accordance with a preferred embodiment of the present invention. FIG. 9 illustrates a message 900 formed by the mapping system 314 in the server 108, as shown in FIG. 3, using the method, as shown in FIG. 8, in accordance with a preferred embodiment of the present invention.

At step 801, the method 800 starts.

At step 802, the method 800 receives the message 600, as shown in FIG. 6, from the data router 106 using the I.P. data format.

At step 803, the method 800 identifies the pin configuration in the message 600.

At step 804, the method 800 identifies the medical device 102-104 responsive to the pin configuration for the medical device field 602. The various makes, models and/or types of medical devices 102-104 corresponding to the various pin configurations are stored in the memory device 310 in the server 108. The mapping system 314 in the server 108 performs an open database connectivity (ODBC) process or a table lookup process to determine the corresponding medical devices 102-104.

At step 805, the method 800 decodes the medical device message field 604 responsive to the identity of the medical device 102-104. Preferably, only one decoder is needed because the messages 600 are received in the I.P. data format. Alternatively, depending on the arrangement of the content of the messages 600 in the I.P. data format, different decoders may be need to interpret the arrangement of the content of the messages 600 responsive to various makes, models and/or types of medical devices 102-104.

At step 806, the method 800 formats the decoded medical device message 902, as shown in FIG. 9, for the information system 110-112 using the information system data format. Different formatting schemes may be employed by the mapping system 314 corresponding the different types of information systems 110-112 intended to receive the formatted message.

At step 807, the method 800 appends additional information 901, as shown in FIG. 9, to the medical device message 902 for the information system 110-112. The additional information includes, without limitation, a person's physical location (e.g., room number and/or bed location in the room) corresponding to the I.P. address of the jack or data router 106, the make and/or model of the medical device that sent the message, a time and/or date stamp of when the message was sent, the person's name corresponding to the I.P. address of the jack or data router 106, and the units of the data being sent, as described above. The mapping system 314 in the server 108 performs an open database connectivity (ODBC) process or a table lookup process, using the map 311 stored in the memory device 310, to determine the appropriate additional information For example, a patient in room and bed location 232-1A is attached to a patient monitoring system 101 that continuously or periodically monitors the patient's pulse rate. The data from the pulse rate-monitoring device (i.e., the medical device) provides an output value of "94". The output value of "94," without including the units of the measurement, does not clearly identify that the output value represents a pulse rate, rather than representing a patient's temperature, for example. In the preferred embodiment of the present invention, when the pulse rate-monitoring device is connected to the data router 106 via the RS232 cable with a pin configuration of 1-4-8, for example, the output value of "94" would be appended with the units of the measurement by the mapping system 314 in the server 108 before being sent on to the information system 110-112.

At step 808, the method 800 sends the formatted message to the information system 110 112 using the information system data format.

At step 809, the method 800 ends.

Figure 10:
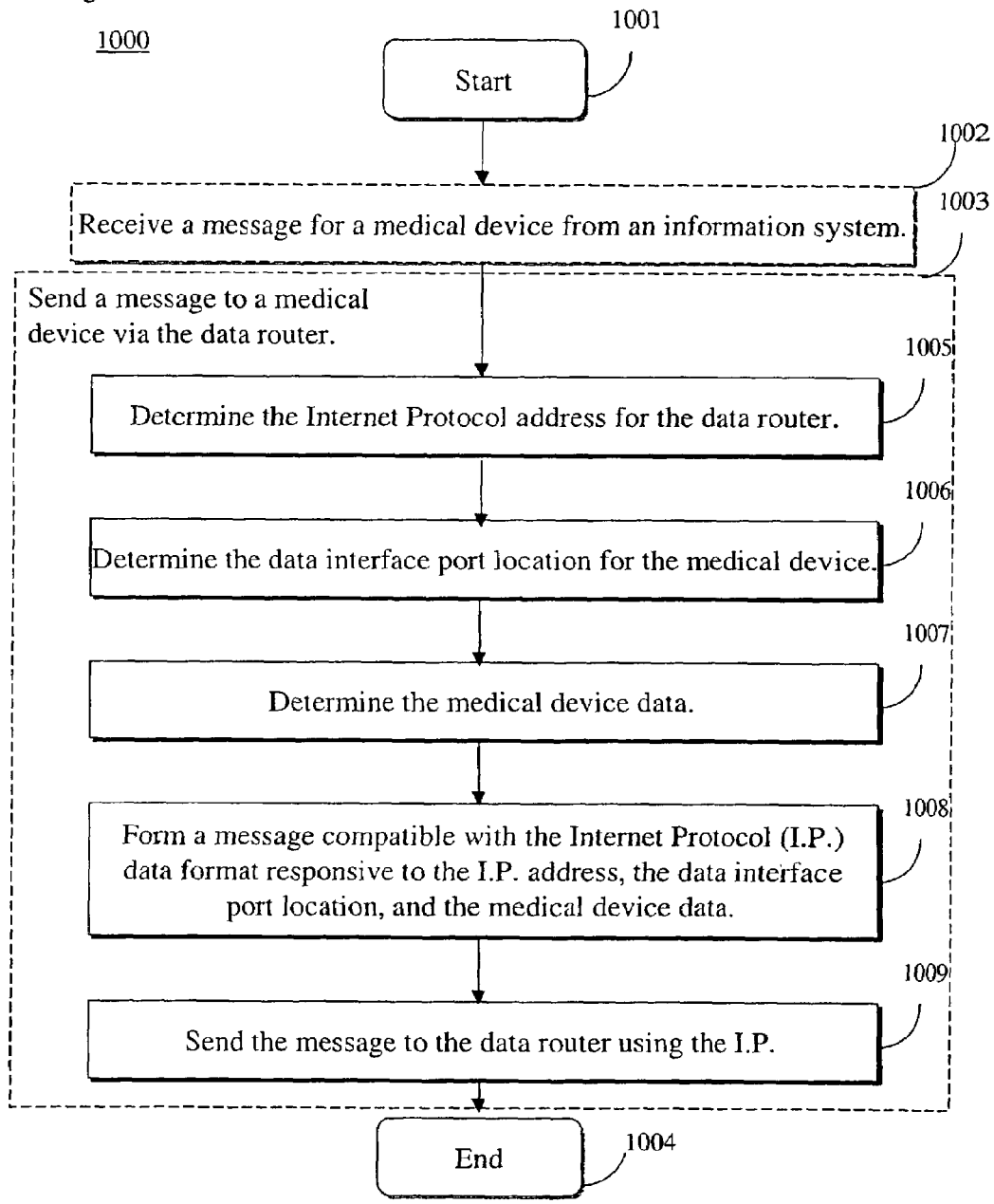
FIG. 10 illustrates a method performed by the message generator in the server, as shown in FIG. 3, in accordance with a preferred embodiment of the present invention.
Figure 11:
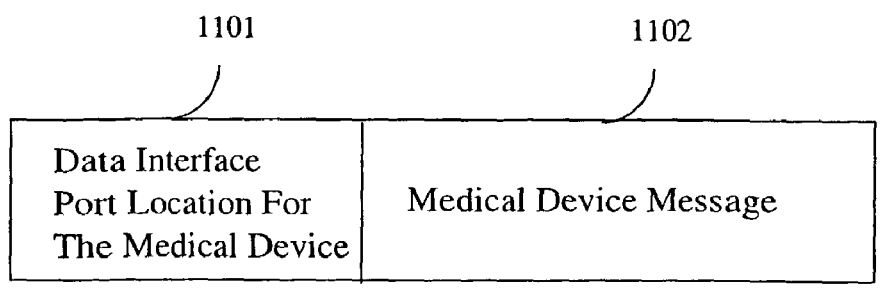
FIG. 11 illustrates a message formed by the message generator in the server, as shown in FIG. 3, using the method, as shown in FIG. 10, in accordance with a preferred embodiment of the present invention.

FIGS. 10 and 11 are described together. FIG. 10 illustrates a method 900 performed by the message generator 318 in the server 108, as shown in FIG. 3, in accordance with a preferred embodiment of the present invention. FIG. 11 illustrates a message 1000 formed by the message generator 318 in the server 108, as shown in FIG. 3, using the method, as shown in FIG. 10, in accordance with a preferred embodiment of the present invention.

At step 1001, the method 1000 starts.

At step 1002, the method 1000 receives a message for a medical device 102-104 from an information system 110-112. This step is optional and therefore shown as a dashed box. Typically, the information system 110-112 will be used only to receive data from the medical devices 102-104, and will not need to send messages back to the medical device 102-104.

At step 1003, the method 900 sends the message 100 to a medical device 102-104 via the data router 106. In the preferred embodiment of the present invention, the message 1100 is an acknowledgement message to notify the medical device that the server 108 received the message 500 (converted and appended to message 600) from the medical device 102-104. Hence, the inbound message 500/600 to the server 108 and the outbound message 1100 from the server 108 provide a handshake scheme to ensure that message that are sent are actually received. However, if a medical device 102-104 does not request or require an acknowledgement message, then the message 1100 is not sent. Whether or not the message 1100 is sent may depend on the particular acknowledgement message. Alternatively, the message 1100 may also represent any other type of message including, without limitation, a test or diagnostic message, and a control message.

At step 1005, the method 1000 determines the I.P. address for the data router 106 responsive to the I.P. address identified by the I.P. address identifier 316. The I.P. address for the data router 106 permits the message 1100 to be routed to the appropriate data router 106.

At step 1006, the method 1000 determines the data interface port location on the data router 106 for the medical device 102-104. The data interface port location on the data router 106 permits the message 1100 to be routed to the appropriate medical device 102-104 connected to the data router 106.

At step 1007, the method 1000 determines the medical device message to be sent to the medical device 102-104. The medical device message is the information that the server 108 desires to transmit to the medical device 102-104, as described above.

At step 1008, the method 1000 forms the message 1100 compatible with the I.P. data format responsive to the I.P. address, the data interface port location, and the medical device message. The message 1100, as shown in FIG. 1100, includes a field 1101 for the data interface port location of the data router 106 and a field 1102 for the medical device message. The particular order of the fields 1101-1102 may vary according to design considerations. In the wireless case, as described above, the message 1100 would also have a field for the I.P. address for the data router 106.

At step 1009, the method 1000 sends the message 1100 to the data router 106 using the I.P. data format.

At step 1010, the method 1000 ends.

FIG. 12 illustrates a method 1200 performed by the server to medical device data router 214, as shown in FIG. 2, in accordance with a preferred embodiment of the present invention.

At step 1201, the method 1200 starts.

At step 1202, the method 1200 receives the message 1100, as shown in FIG. 11, from the server 108 responsive to receiving and identifying the field 1101 having the I.P. address of the data router 106 in the message 1100.

At step 1203, the method 1200 identifies the data interface port location on the data router 106 for the medical device 102-104 responsive to receiving and identifying the field 1102 having the data interface port location in the message 1100.

At step 1204, the method 1200 identifies the medical device message responsive to receiving and identifying the field 1103 having the medical device message in the message 1100.

At step 1205, the method 1200 forms a message 500, as shown in FIG. 5, for a medical device 102-104 that is compatible with the medical device data format. The message 500 is formed by removing the fields 1001 and 1002 for the I.P. address and the data interface port location, respectively, and by converting medical device message from the I.P. data format to the medical device data format. Hence, the message 500, as shown in FIG. 5, uses the same medical device data format used for messages being sent from or sent to a particular medical device 102-104.

At step 1206, the method 1200 sends the message to the medical device 102-104 responsive to the data interface port location for the medical device 102-104.

At step 1207, the method 1200 ends.

Hence, while the present invention has been described with reference to various illustrative embodiments thereof, the present invention is not intended that the invention be limited to these specific embodiments. Those skilled in the art will recognize that variations, modifications and combinations of the disclosed subject matter can be made without departing from the spirit and scope of the invention as set forth in the appended claims.

What is claimed is:

1. A method for processing data acquired from multiple medical devices located at one of a plurality of patient bed stations, comprising the activities of:
bi-directionally communicating with a plurality of medical devices in automatically acquiring data, including patient related information, and acquisition device type identifier information from one or more of said plurality of medical devices using a communication protocol automatically selected from a plurality of communication protocols associated with different medical devices;

incorporating said acquisition device type identifier information derived from acquired data into a message in an Internet compatible format for communication to a remote device;

identifying a patient associated with a patient bed station from a database associating patients and patient bed stations; and bi-directionally communicating via a data router with said remote device to convey said acquisition device type identifier information to said remote device in the Internet compatible format message, said data router having a predetermined source Internet communication address usable by said remote device to identify a physical location of said data router and an acquisition device type identifier, associated with said individual medical device and being conveyed in said Internet compatible format message, being usable by said remote device to identify an individual medical device of said plurality of medical devices providing message content to said remote device via said data router in said Internet compatible format message, said data router having a source physical location being determinable from a map associating Internet communication addresses and source physical locations.

2. A method according to claim 1, wherein said source physical location comprises said patient bed station and said activity of incorporating said acquisition device type identifier information into said Internet compatible format message includes converting information derived from said acquired data from a first format to said Internet compatible format for output in response to a format conversion selection command and said remote device comprises a particular destination healthcare information system and including the step of at least one of, (a) adding additional information to, and (b) deleting information from, said Internet compatible format message to provide a message compatible with said particular destination healthcare information system.

3. A method according to claim 1, including the activity of:

automatically acquiring said acquisition device type identifier in response to a communication connection being established supporting bi-directional communication with one of said plurality of medical devices and storing an identifier identifying one of said plurality of medical devices, said identifier comprising at least one of, (a) a port identifier identifying a port receiving data from said one of said plurality of medical devices, (b) a code in data from said one of said plurality of medical devices identifying said one of said plurality of medical devices and (c) a pin configuration associated with a port receiving data from said one of said plurality of medical devices and identifying said one of said plurality of medical devices.

4. A method according to claim 1, wherein automatically acquiring said acquisition device type identifier information in response to a communication connection being established supporting bi-directional communication with one of said plurality of medical devices and said communication protocol comprises at least one of, (a) RS232 protocol, (b) Ethernet protocol, (c) Medical Interface Bus (MIB) compatible protocol, (c) an Internet compatible protocol, (d) a Local Area Network (LAN) protocol, (e) a Wide Area Network (WAN) protocol, (f) an IEEE bus compatible protocol and (g) an HL7 (Health Level Seven) protocol.

5. A method according to claim 1, including the activity of:

incorporating together with said acquisition device type identifier information in said Internet compatible format message, at least one of:

(a) an identifier identifying a system employing said method, and (b) an identifier identifying a patient related information type.

6. A method according to claim 1, including the activity of:

receiving an acknowledgement communication from said remote device indicating receipt of said message by said remote device.

7. A method according to claim 6, including the activity of:

using an identifier identifying one of said plurality of medical devices in sending an acknowledgement communication to said one of said plurality of medical devices in response to receiving said acknowledgement from said remote device.

8. A method according to claim 1, including the activities of:

automatically acquiring said acquisition device type identifier information from said one of said plurality of medical devices without initiating interrogation of said one of said plurality of medical devices to obtain said device type identifier.

9. A method according to claim 1, wherein said source Internet communication address comprises at least one of (a) an Internet Protocol (IP) address, (b) a Universal Resource Locator (URL) and (c) an Email address.

10. A method for processing an Internet compatible format message including data acquired from at least one of a plurality of medical devices located at one of a plurality of patient bed stations, comprising the activities of:

receiving an Internet compatible format message incorporating an acquisition device type identifier associated with an individual medical device of a plurality of medical devices, said individual medical device providing message content from a patient bed station via a data router, said data router having an associated Internet communication address;

deriving said source Internet communication address from said Internet compatible format message;

identifying a physical location of said data router comprising a patient bed station in response to said derived Internet communication address by using a map associating Internet communication addresses and physical locations of data routers;

using said acquisition device type identifier to identify said individual medical device of said plurality of medical devices providing message content via said data router in said Internet compatible format message using a database of information indicating device type and associated device type identifier; and identifying a patient associated with said patient bed station from a database associating patients and patient bed stations.

11. A method according to claim 10, including the activity of:

converting received data in said Internet compatible format message from a first format to a different second format for output in response to a user format conversion selection command.

12. A method according to claim 10, including the activity of:
   interpreting said Internet compatible format message in response to a medical device type identified using said acquisition device type identifier.

13. A method according to claim 10, wherein said source Internet communication address comprises at least one of: (a) an Internet Protocol (IP) address, (b) a Universal Resource Locator (URL) and (c) an Email address.

14. A system for processing data acquired from multiple medical devices located at one of a plurality of patient bed stations, comprising:
   a first data interface for bi-directionally communicating with a plurality of medical devices in acquiring data, including patient related information, and acquisition device type identifier information from one or more of said plurality of medical devices using a communication protocol automatically selected from a plurality of communication protocols associated with different medical devices;
   a second data interface for bi-directionally communicating via a data router with a remote device to convey said acquisition device type identifier information to said remote device in an Internet compatible format message, said data router having a predetermined source Internet communication address usable by said remote device to identify a physical location of said data router and an acquisition device type identifier, associated with said individual medical device and being conveyed in said Internet compatible format message, said acquisition device type identifier information being usable by said remote device to identify an individual medical device of said plurality of medical devices providing message content to said remote device via said data router in said Internet compatible format message, said data router having a source physical location being determinable from a map associating Internet Protocol addresses and source physical locations; and
   a data processor coupled to said first data interface and said second data interface for incorporating said acquisition device type identifier information into said Internet compatible format message for communication to said remote device and for identifying a patient associated with a patient bed station from a database associating patients and patient bed stations.

15. A system for processing an internet compatible format message including data acquired from at least one of a plurality of medical devices located at one of a plurality of patient bed stations, comprising:
   a data interface for receiving an Internet compatible format message incorporating an acquisition device type identifier associated with an individual medical device of a plurality of medical devices, said individual medical device providing message content from a patient bed station via a data router, said data router having an associated Internet communication address; and
   a data processor for,
      deriving said Internet communication address from said Internet compatible format message,
      identifying a physical location of said data router comprising a patient bed station, in response to said derived Internet communication address by using a map associating Internet communication addresses and physical locations of data routers,
      using said acquisition device type identifier to identify said individual medical device of said plurality of medical devices providing message content via said data router in said Internet compatible format message using a database of information indicating device type and associated device type identifier and
      identifying a patient associated with said patient bed station from a database associating patients and patient bed stations.

16. A system according to claim 14, wherein
   said first data interface automatically acquires said acquisition device type identifier information in response to a communication connection being established supporting said bi-directional communication with one of said plurality of medical devices.

17. A system according to claim 15, wherein
   said acquisition device type identifier is automatically acquired from one of said plurality of medical devices in response to a communication connection being established supporting bi-directional communication with said one of said plurality of medical devices.

18. A method for processing data acquired from multiple medical devices located at one of a plurality of patient bed stations, comprising the activities of:
   bi-directionally communicating with a plurality of medical devices in automatically acquiring data, including patient related information, and acquisition device type identifier information from one or more of said plurality of medical devices using a communication protocol automatically selected from a plurality of communication protocols associated with different medical devices;
   incorporating said acquisition device type identifier information derived from acquired data into a message in an Internet compatible format for communication to a remote device;
   bi-directionally communicating via a data router with said remote device to convey said acquisition device type identifier information to said remote device in the Internet compatible format message, said acquisition device type identifier information being usable by said remote device to identify a physical location of said data router and an acquisition device type identifier, associated with said individual medical device and being conveyed in said Internet compatible format message, being usable by said remote device to identify an individual medical device of said plurality of medical devices providing message content to said remote device via said data router in said Internet compatible format message, said data router source physical location being derivable from a map associating Internet communication addresses and source physical locations;
   identifying a patient associated with a patient bed station from a database associating patients and patient bed stations; and
   interpreting said Internet compatible format message in response to a medical device type identified from said acquisition device type.

19. A system according to claim 18, including the activity of
   receiving an acknowledgement communication from said remote device indicating receipt of said message by said remote device.

* * * * *